United States Patent

Kacian et al.

[11] Patent Number: 5,888,729
[45] Date of Patent: *Mar. 30, 1999

[54] **OLIGONUCLEOTIDE PROBES AND METHODS FOR DETECTING *STREPTOCOCCUS PNEUMONIAE***

[75] Inventors: Daniel L. Kacian; Diane L. McAllister; Sherrol H. McDonough; Nanibhushan Dattagupta, all of San Diego, Calif.

[73] Assignee: Gen-Probe Incorporated, San Diego, Calif.

[*] Notice: The term of this patent shall not extend beyond the expiration date of Pat. No. 5,554,516.

[21] Appl. No.: 486,915

[22] Filed: Jun. 7, 1995

Related U.S. Application Data

[63] Continuation of Ser. No. 162,836, Dec. 2, 1993, Pat. No. 5,554,516, which is a continuation of Ser. No. 879,686, May 6, 1992, abandoned.

[51] Int. Cl.⁶ .............................. C12Q 1/68; C12P 19/34; C07H 21/04
[52] U.S. Cl. .................... 435/6; 435/91.2; 435/91.21; 435/91.5; 435/91.51; 536/24.1; 536/24.33
[58] Field of Search ................. 435/6, 91.2, 91.21, 435/91.5, 91.51, 91.53; 536/24.33, 24.1; 935/17, 18, 8, 77, 78

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis et al. | 435/91.2 |
| 4,786,600 | 11/1988 | Kramer et al. | 435/320.1 |
| 4,800,159 | 1/1989 | Mullis et al. | 435/91.2 |
| 4,876,197 | 10/1989 | Duck et al. | 435/172.3 |
| 5,030,557 | 7/1991 | Hogan | 435/6 |

FOREIGN PATENT DOCUMENTS

| | | |
|---|---|---|
| 559709 | 2/1988 | Canada. |
| 0200362 | 3/1986 | European Pat. Off.. |
| 0201184 | 12/1986 | European Pat. Off.. |
| 0229701 | 7/1987 | European Pat. Off.. |

(List continued on next page.)

OTHER PUBLICATIONS

Rogers et al., Proceedings National Academy of Sciences (1985) 82:1160–1164.
Davis et al., Journal of Clinical Microbiology (1991) 29:2193–2196.
Fahy et al., PCR Methods and Applications (Aug. 1991) 1:25–33.
Kwoh et al., American Biotechnology Laboratory (1990) 18: 14–25.
Bethesda Research Laboratories Catalogue & Reference Guide, Bethesda Research Laboratories, Bethesda, MD p. 37 (1988).
Boehringer Mannheim Catalog, pp. 69–70 (1990/1991).
Both et al., "A general strategy for cloning double–stranded RNA: nucleotide sequence of the Simian–11 rotavirus gene 8," *Nucleic Acids Research* 10:7075 (1982).
Cashdollar et al., "Cloning the Double–stranded RNA Genes of a Reovirus: Sequence of the cloned S2 gene," *Proc. Natl. Acad. Sci. USA* 79:7644–7648 (1982).

(List continued on next page.)

*Primary Examiner*—Carla J. Myers
*Attorney, Agent, or Firm*—Lyon & Lyon LLP

[57] ABSTRACT

A method, composition and kit for amplifying a target nucleic acid sequence under conditions of substantially constant temperature, ionic strength, and pH and using only a single promoter-primer. To effect the amplification, a supply of a single promoter-primer having a promoter and a primer complementary to the 3'-end of the target sequence, and a reverse transcriptase and an RNA polymerase are provided to a mixture including the target sequence; the amplification proceeds accordingly. The invention is useful for generating copies of a nucleic acid target sequence for purposes that include assays to quantitate specific nucleic acid sequences in clinical, environmental, forensic and similar samples, cloning and generating probes.

20 Claims, 1 Drawing Sheet

FOREIGN PATENT DOCUMENTS

| | | |
|---|---|---|
| 0300796 | 1/1989 | European Pat. Off. . |
| 0320308 | 6/1989 | European Pat. Off. . |
| 0329822 | 8/1989 | European Pat. Off. . |
| 0398677 | 5/1990 | European Pat. Off. . |
| 0373960 | 6/1990 | European Pat. Off. . |
| 0408295 | 1/1991 | European Pat. Off. . |
| 0427073 | 5/1991 | European Pat. Off. . |
| 0461065 | 6/1991 | European Pat. Off. . |
| 2651505 | 9/1989 | France . |
| 2659086 | 7/1990 | France . |
| 8803957 | 6/1988 | WIPO . |
| 8810315 | 12/1988 | WIPO . |
| 8901050 | 2/1989 | WIPO . |
| 8902439 | 3/1989 | WIPO . |
| 8902476 | 3/1989 | WIPO . |
| 8906700 | 7/1989 | WIPO . |
| 8706270 | 10/1989 | WIPO . |
| 9014439 | 11/1990 | WIPO . |
| 9102818 | 3/1991 | WIPO . |
| 9110746 | 7/1991 | WIPO . |
| 9115601 | 10/1991 | WIPO . |

OTHER PUBLICATIONS

Cox et al., "The 16S ribosomal RNA of *Mycobacterium leprae* contains a unique sequence which can be used for identification by the polymerase chain reaction," *J. Med. Microbiol.* 35:284–290 (1991).

Davis and Fuller, "Direct Identification of Bacterial Isolates in Blood Cultures by Using a DNA Probe" *Journal of Clinical Microbiology* 29(10):2193–2196 (1991).

European Search Report for Appln. No. 90307503.4 dated Jul. 12, 1991.

Fahy et al, "Self–sustained Sequence Replication (3SR): An Isothermal Transcription–based Amplification System Alternative to PCR," *PCR Methods and Applications* 1:25–33 (1991).

Gingeras et al., U.S. Patent Application Serial No. 07/202, 978 filed Jun. 6, 1988, "Transcription–Based Nucleic Acid Amplification/Detection Systems".

Grachev et al., "Oligonucleotides complementary to a promoter over the region –8 . . . +2 as transcription primers for *E. coli* RNA polymerase," *Nucleic Acids Research* 12:8509 (1984).

Guatelli et al., "Isothermal, in vitro amplification of nucleic acids by a multienzyme reaction modeled after retroviral replication," *Proc. Natl. Acad. Sci. USA* 87:1874–1878 (1990).

Gubler, *Guide to Molecular Cloning Techniques,* Academic Press, New York, NY, p. 330 (1987).

Hayes, "The Genetics of Bacteria and their Viruses," John Wiley & Sons Inc., 2nd ed. pp. 239–257, New York (1964).

Hentosh et al., "Polymerase Chain Reaction Amplification of Single–Stranded DNA Containing a Base Analog, 2–Chloroadenine," *Analytical Biochemistry* 201:277–281 (1992).

Hogan et al., Gene Bank Accession No. N80793 (Nov. 30, 1990).

Joyce, "Amplification, Mutation and Selection of Catalytic RNA," *Gene* 82:83–87 (1989).

Khorana, "Total Synthesis of a Gene," *Science,* 203:614–25 (1979).

Krug and Berger, "Ribonuclease H activities associated with viral reverse transcriptases are endocucleases," *Proc. Natl. Acad. Sci. USA* 86:3539–3543 (1989).

Krug and Berger, "First–Strand cDNA Synthesis Primed with Oligo(dT)," (Methods in Enzymology) *Guide to Molecular Cloning Techniques,* Berger and Kimmel, eds., (Academic Press:NY) 152:316–325 (1987).

Kupper et al., "Promoter–dependent transcription of TRN-$A_I^{Tyr}$ genes using DNA fragments produced by restriction enzymes," *Proc. Natl. Acad. Sci. USA* 72:4754 (1975).

Kwoh et al., "Target amplification systems in nucleic acid–based diagnostic approaches," *American Biotechnology Laboratory* 18:14–25 (1990).

Kwoh et al., "Transcription–based amplification system and detection of amplified human immunodeficiency virus type 1 with a bead–based sandwich hybridization format," *Proc. Natl. Acad. Sci. USA* 86:1173–1177 (1989).

Lomonossoff, et al., "The Location of the First AUG Condons in Cowpea Mosaic Virus RNAs," *Nucleic Acids Research,* 10,16:4861–72 (1982).

Lowary et al., "A Better Way to Make RNA for Physical Studies," Structure & Dynamics of RNA, Nato ASI Series Knippenberg, eds. (New York: Plenum Press, 1986 vol. 110.

Milligan et al., "Oligoribonucleotide synthesis using T7 RNA polymerase and synthetic DNA templates," *Nucleic Acids Research* 15:8783–98 (1987).

Mullis et al., "Specific Synthesis of DNA in Vitro via a Polymerase–Catalyzed Chain Reaction," *Methods in Enzymology* 155:335 (1987).

Mullis and Faloona, "Specific Synthesis of DNA in Vitro via a Polymerase–Catalyzed Chain Reaction," *Methods in Enzymology* 155:355–349 (1987).

Murakawa et al., "Direct Detection of HIV–1 RNA from AIDS and ARC Patient Samples," *DNA* 7:287–295 (1988).

Okayama and Berg, "High–Efficiency Cloning of Full–Lenth cDNA," *Molecular and Cellular Biology* 2:161–170 (1982).

Oyama et al., "Intrinsic Properties of Reverse Transcriptase in Reverse Transcription," *J. Biol. Chem.* 264:18808–18817 (1989).

Rogers et al., "Construction of the mycoplasma evolutionary tree from 5S rRNA sequence data," *Proc. Natl. Acad. Sci. USA* 82:1160–1164 (1985).

Rossi et al., "An Alternate Method for Synthesis of Double–stranded DNA segments," *J. Biol. Chem.* 257:9226 (1982).

Sorge and Blinderman, "ExoMeth sequencing of DNA: Eliminating the Need for Subcloning and Oligonucleotide Primers," *Proc. Natl. Acad. Sci. USA* 86:9208–9212 (1989).

Stent, *Molecular Biology of Bacterial Viruses,* W.H. Freeman & Company, San Francisco, pp. 157–163 (1963).

Tyagi et al., "Molecular Biology—Transfer RNA genes in mycobacteria: organization and molecular cloning," *Trop. Med. Parasitol,* 41:294–296 (1990).

Walker et al., "Isothermal in vitro amplification of DNA by a restriction enzyme/DNA polymerase system," *Proc. Natl. Acad. Sci. USA* 89:392–396 (1992).

Watson & Crick, "Genetical Implications of the Structure of Deoxyribonucleic Acid," *Nature* 171:964–967 (1953).

Watson and Crick, "Molecular Structure of Nucleic Acids," *Nature* p. 737 (Apr. 25, 1953).

Wilk et al., "Backbone–modified Oligonucleotides Containing a Butanediol–1,3 Moiety as a 'Vicarious Segment' for the Doxyribosyl Moiety—Synthesis and Enzyme Studies," *Nucleic Acids Research* 18:2065–2068 (1990).

Zoller and Smith, "Oligonucleotide–Directed Mutagenesis of DNA Fragments Cloned into M13 Vectors," *Methods in Enzymology* 100:468–500 (1983).

OLIGONUCLEOTIDE PROBES AND METHODS FOR DETECTING *STREPTOCOCCUS PNEUMONIAE*

This is a continuation of application Ser. No. 08/162,836, filed Dec. 2, 1993, Now U.S. Pat. No. 5,554,516, which is a continuation of U.S. application Ser. No. 07/879,686, filed May 6, 1992, abandoned, both of these applications are hereby incorporated by reference herein in their entirety (including the drawings).

FIELD OF THE INVENTION

The field of the present invention is increasing the number of copies (or amplifying) of a specific nucleic acid sequence or "target sequence." The target sequence may be present either alone or as a component, large or small, of an homogeneous or heterogeneous mixture of nucleic acids. The mixture of nucleic acids may be that found in a sample taken for diagnostic testing, environmental testing, for research studies, for the preparation of reagents or materials for other processes such as cloning, or for other purposes.

The selective amplification of specific nucleic acid sequences is of value in increasing the sensitivity of diagnostic and environmental assays, and other uses, while maintaining specificity, increasing the sensitivity, convenience, accuracy and reliability of a variety of research procedures, and providing ample supplies of specific oligonucleotides for various purposes.

The present invention is particularly suitable for use in environmental and diagnostic testing due to the convenience with which it may be practiced.

BACKGROUND OF THE INVENTION

The detection and/or quantitation of specific nucleic acid sequences is an increasingly important technique for identifying and classifying microorganisms, diagnosing infectious diseases, detecting and characterizing genetic abnormalities, identifying genetic changes associated with cancer, studying genetic susceptibility to disease, and measuring response to various types of treatment. Such procedures have also found expanding uses in detecting and quantitating micro-organisms in foodstuffs, environmental samples, seed stocks, and other types of material where the presence of specific microorganisms may need to be monitored. Other applications are found in the forensic sciences, anthropology, archaeology, and biology where measurement of the relatedness of nucleic acid sequences has been used to identify criminal suspects, resolve paternity disputes, construct genealogical and phylogenetic trees, and aid in classifying a variety of life forms.

A common method for detecting and quantitating specific nucleic acid sequences is nucleic acid hybridization. This method is based on the ability of two nucleic acid strands which contain complementary or essentially complementary sequences to specifically associate, under appropriate conditions, to form a double-stranded structure. To detect and/or quantitate a specific nucleic acid sequence (known as the "target sequence"), a labelled oligonucleotide (known as a "probe") is prepared which contains sequences complementary to those of the target sequence. In a process commonly known as "screening," the probe is mixed with a sample suspected of containing the target sequence, and conditions suitable for hybrid formation are created. The probe hybridizes to the target sequence if it is present in the sample. The probe-target hybrids are then separated from the single-stranded probe in one of a variety of ways. The amount of label associated with the hybrids is then measured as an indication of the amount of target sequence in the sample.

The sensitivity of nucleic acid hybridization assays is limited primarily by the specific activity of the probe, the rate and extent of the hybridization reaction, the performance of the method for separating hybridized and unhybridized probe, and the sensitivity with which the label can be detected. Under the best conditions, direct hybridization methods such as those described above can detect about $1\times10^5$ to $1\times10^6$ target molecules. However, the most sensitive procedures may lack many of the features required for routine clinical and environmental testing such as speed, convenience, and economy. Furthermore, the sensitivities of even the most sensitive procedures may not be sufficient for many desired applications.

As a result of the interactions among the various components, and the component steps of this type of assay, there is almost always an inverse relationship between sensitivity and specificity. Thus, steps taken to increase the sensitivity of the assay (such as increasing the specific activity of the probe) may result in a higher percentage of false positive test results. The linkage between sensitivity and specificity has been a significant barrier to improving the sensitivity: of hybridization assays. One solution to this problem would be to specifically increase the amount of target sequence present using an amplification procedure. Amplifying a unique portion of the target sequence without amplifying a significant portion of the information encoded in the remaining sequences of the sample could give an effective increase in sensitivity while at the same time not compromising specificity.

A method for specifically amplifying nucleic acid sequences termed the "polymerase chain reaction" or "PCR" has been described by Mullis, et al. (See U.S. Pat. Nos. 4,683,195, 4,683,202 and 4,800,159 and European patent applications 86302298.4, 86302299.2, and 87300203.4 and *Methods in Enzymology*, Volume 155, 1987, pp. 335–350). The PCR procedure uses repeated cycles of primer dependent nucleic acid synthesis occurring simultaneously using each strand of a complementary sequence as a template. In the PCR procedure, copies of both strands of a complementary sequence are synthesized. In order to make the PCR convenient, programmable thermal cycling instruments are required.

The PCR procedure has been coupled to RNA transcription by incorporating a promoter sequence into one of the primers used in the PCR reaction and then, after amplification by the PCR procedure for several cycles, using the double-stranded DNA as template for the transcription of single-stranded RNA. (See, e.g., Murakawa et al., DNA 7:287–295 (1988)).

Other methods for amplification of a specific nucleic acid sequence comprise a series of cycles of primer hybridization, extending steps and denaturing steps to provide an intermediate double stranded DNA molecule containing a promoter sequence through the use of a promoter sequence-containing primer. The double stranded DNA is used to produce multiple RNA copies of the target sequence. The resulting RNA copies can be used as target sequences to produce further copies and multiple cycles can be performed. (See, e.g., Burg, et al., WO 89/1050; Gingeras, et al., WO 88/10315 (sometimes called "transcription amplification system" or TAS); EPO Application No. 89313154 to Kacian and Fultz; EPO Application No. 88113948.9 to Davey and Malek; Malek, et al. WO91/02818).

Walker, et al., Proc. Natl. Acad. Sci. (USA) 89:392–396 (Jan. 1992), not admitted to be prior art, describes an oligonucleotide driven amplification method for use with a DNA template, using a restriction endonuclease to produce the initial target sequences and an enzyme to nick the DNA/DNA complex in order to enable an extension reaction and therefore amplification. Becker, et al., EPO Application No. 88306717.5, describes an amplification method in which a primer is hybridized to the target sequence and the resulting duplex is cleaved prior to the extension reaction and amplification; in the case where the primer extends past the region of hybridization, it requires cleavage prior to the extension and the primer must be blocked at its 3'-end to prevent any unwanted extension reactions from occurring prior to amplification. Kramer, et al., U.S. Pat. No. 4,786, 600 describe a method of producing large numbers of copies of a probe sequence in an RNA target sequence using Qβ replicase. Urdea, WO 91/10746, describes a signal amplification method that incorporates a T7 promoter sequence.

Other methods of amplifying nucleic acid include the ligase chain reaction (LCR), described in European Patent Publication 320,308, in which at least four separate oligoprobes are used; two of the oligoprobes hybridize to opposite ends of the same target strand in appropriate orientation such that the third and fourth oligoprobes may hybridize with the first and second oligoprobes to form, upon ligation, connected probes that can be denatured and detected. Another method is that described in EPO Publication No. 0 427 073 A2, published May 15, 1991 and not admitted to be prior art, in which a palindromic probe able to form a hairpin and having a functional promoter region in the hairpin is hybridized to a target sequence, then ligated to a second oligonucleotide hybridized to the target sequence such that RNA transcripts may be made.

Still other methods include oligonucleotide synthesis and cloning.

SUMMARY OF THE INVENTION

The present invention is directed to synthesizing multiple copies of a target nucleic acid sequence without the need to modify reaction conditions such as temperature, pH, or ionic strength, and without the need to add multiple, different primers or promoters, nor enzymes other than polymerases, which may also have RNAse H activities.

The present invention may be used as a component of assays to detect and/or quantitate specific nucleic acid target sequences in clinical, environmental, forensic, and similar samples or to produce large numbers of copies of DNA and/or RNA of specific target sequence for a variety of uses. The present invention may also be used to produce multiple DNA or RNA copies of a nucleic acid target sequence for cloning or to generate probes or to produce RNA or DNA copies for sequencing.

The present method features incubating a mixture consisting essentially of a nucleic acid target sequence (DNA or RNA) with one or more oligonucleotides known as "promoter-primers" that have a "complexing" sequence (i.e., a primer) sufficiently complementary to the 3'-end of a target sequence to hybridize at or near the 3'-end of the target sequence. The promoter-primer also includes, located 5' to the complexing sequence, a promoter for an RNA polymerase.

By "at or near" is simply meant to indicate the 3'-end of the target itself, and not necessarily the whole RNA or DNA-molecule which is to be detected. For example, the "target" may be a small central portion of an RNA molecule within an otherwise large RNA molecule.

By "one or more" it is meant that the promoter-primers added to the reaction mixture are sufficiently similar that they are able to bind to approximately the same target sequence at approximately the same position (plus or minus about 10 bases, on the same strand) such that the amplification of the instant invention may go forward. This does not exclude providing other oligonucleotides to the mixture, for example "helper" oligonucleotides that aid hybridization of the promoter-primers.

By "consisting essentially of" as used above, it is meant that the mixture has all of the necessary reactants and reagents. However, such a mixture may also contain enzymes or other substituents that do not qualitatively affect the amplification of the invention, and the mixture may contain other promoter-primers for the same target sequence or "helper" oligonucleotides. A "helper" oligonucleotide is a nucleic acid sequence that assists complexing between the promoter-primer, or other complexing nucleic acid such as a probe, and the target sequence, and will be determined by the actual sequence at the 3'-end of the target sequence. Such helper oligonucleotides are used in a manner equivalent to hybridization helper oligonucleotides described by Hogan et al., U.S. Pat. No. 5,030,557, namely by aiding binding of the promoter-primer to its target nucleic acid even if that target nucleic acid has significant secondary structure. Despite the similarity in use of such helper oligonucleotides it is surprising that such helper oligonucleotides could be used in an amplification protocol without adverse effect on the efficiency of these rocedures.

The promoter-primer and the target sequence are subjected to conditions whereby a promoter-primer/target sequence hybrid is formed and DNA synthesis can be initiated. It is believed that in this reaction, the 3'-end of the target sequence is extended in a DNA extension reaction from a location adjacent the hybridized complex between the complexing sequence and the target sequence. The promoter sequence is the template for this extension reaction, which produces a first DNA extension product and thereby a double stranded promoter sequence. The 3'-end of the promoter-primer may also serve as a primer, for a second DNA extension reaction, which reaction uses the target sequence as a template and results in a double stranded nucleic acid complex; the complex is a DNA/RNA complex if an RNA target sequence is used, and a DNA/DNA complex if a DNA target sequence is used.

The first DNA extension product is then used by an RNA polymerase that recognizes the promoter of the promoter-primer, to produce multiple RNA copies of the target sequence. Surprisingly, in the case of an RNA/DNA complex or RNA alone comprising the target sequence, a DNA-dependent RNA polymerase, such as T7 RNA polymerase, is able to "read" the RNA/DNA complex or RNA and produce single stranded RNA, and is therefore effective in the present invention.

In preferred embodiments, the promoter-primer has a modification that may comprise a modified nucleotide at or near its 3'-end that inhibits or prohibits nucleic acid extension in that direction. It is surprising that the invention may be performed with the 3'-end of the promoter-primer modified, and it is particularly surprising that using a mixture of a modified and an unmodified promoter-primer (or two differently modified promotor-primers) results in a higher efficiency amplification, and therefore a higher copy number, than use of an unmodified or modified promoter-primer alone. Methods for creating such useful modifications to prevent or decrease primer extension are known in the art.

Where the target sequence comprises DNA or RNA, a further aspect of the present invention includes generation of a 3'-end of the target sequence by chemical or enzymatic degradation or processing, so that extension of the 3'-end of the target sequence along the promoter region of the promoter-primer may proceed. Such generation may be performed by, for example, the action of RNase H on an RNA:DNA hybrid (e.g., a DNA promoter-primer and an RNA target hybrid), treatment with exonucleases, and digestion with specific restriction endonucleases (e,g., for a DNA target) or ribozymes (e.g., with an RNA or DNA target).

In other preferred embodiments, the present invention features inclusion of one or more "helper" oligonucleotides in the reaction composition.

In yet other preferred embodiments, the 5'-end of the target strand of nucleic acid may be defined so as to stop either the extension reaction or the transcription reaction. Methods to effect such definition are known in the art and may include complexing an appropriate sequence of nucleic acid (e.g., an oligonucleotide) to the 5'-end of the target sequence, or modification of the 5-end of the target sequence.

The present invention also features a composition consisting essentially of a target sequence, a promoter-primer, an RNA polymerase, a DNA polymerase and/or a reverse transcriptase and reagent and buffer conditions sufficient to allow amplification. In another embodiment, the promoter-primer includes both modified and unmodified 3'-ends. The invention also features a composition including a mixture of modified and unmodified promoter-primers and/or a mixture of different promoter-primers suitable for use in this invention.

In one example of a typical assay featuring the present invention, a sample of target nucleic acid to be amplified is mixed with a buffer concentrate containing appropriate buffer, salts, magnesium, nucleotide triphosphates, one or more promoter-primers, dithiothreitol, and spermidine. The reaction is then optionally incubated near 100° C. to denature any secondary structure. (This step is unnecessary if the target is single-stranded RNA, and the promoter-primer is also single-stranded.) After cooling to room temperature, reverse transcriptase and RNA polymerase are added and the reaction is incubated for a time span from minutes to hours at a suitable constant temperature between, e.g., 37° C. to 42° C., at which the enzymes are active. The reaction can then be assayed by adding a probe solution, incubating 10–30 minutes at 60° C., adding a solution to selectively hydrolyze the unhybridized probe, incubating the reaction for 5–10 minutes at 60° C., and measuring the remaining chemiluminescence in a luminometer, as described by Arnold, et al., PCT US88/02746, the disclosure of which is incorporated herein by reference, and is referred to as the "HPA" method. The products of the methods of the present invention may be used in many other assay systems, or for other uses, known to those skilled in the art.

The present invention further features a kit that incorporates the components of the invention and makes possible convenient performance of the invention. Such a kit may also include other materials that would make the invention a part of other procedures, and may also be adaptable for multi-well technology.

Definitions

As used herein, the following terms have the following meanings unless expressly stated to the contrary.
A. Nucleic Acid.

"Nucleic acid" means either RNA or DNA, along with any nucleotide analogues or other molecules that may be present in the sequence and that do not prevent performance of the present invention.

B. Template.

A "template" is a nucleic acid molecule that is able to be copied by a nucleic acid polymerase. A template may be either RNA or DNA, and may be any of single-stranded, double-stranded or partially double-stranded, depending on the polymerase. The synthesized copy is complementary to the template.
C. Primer.

A "primer" is an oligonucleotide that is sufficiently complementary to a template so that it hybridizes (by hydrogen bonding or hybridization under hybridizing conditions, e.g., stringent conditions) with the template to give a primer/template complex suitable for initiation of synthesis by a DNA polymerase, such as a reverse transcriptase, and which is extended by the addition of covalently bonded bases linked to its 3' end that are complementary to the template. The result is a primer extension product. Virtually all DNA polymerases (including reverse transcriptases) that are known require complexing of an oligonucleotide to a single-stranded template ("priming") to initiate DNA synthesis. Under appropriate circumstances, a primer may be a part of a promoter-primer. Such primers are generally between 10 and 100 bases in length, preferably between 20 and 50 bases in length.
D. Promoter or Promoter Sequence.

A "promoter" or "promoter sequence" is a specific nucleic acid sequence that is recognized by a DNA-dependent RNA polymerase ("transcriptase") as a signal to bind to a nucleic acid molecule and begin the transcription of RNA at a specific site. For binding, such transcriptases generally require that the promoter and its complement be double-stranded; the template portion need not be double-stranded. Individual DNA-dependent RNA polymerases recognize a variety of different promoter sequences that can vary markedly in their efficiency of promoting transcription. When an RNA polymerase binds to a promoter sequence to initiate transcription, that promoter sequence is not part of the sequence transcribed. Thus, the RNA transcripts produced thereby will not include the promoter sequence.
E. Promoter-primer.

A promoter-primer comprises a promoter and a primer. It is an oligonucleotide that is sufficiently complementary to the 3'-end of a target nucleic acid sequence to complex at or near the 3'-end of that target nucleic acid sequence, which means that the promoter-primer complexes near enough to the end of the target sequence to allow amplification of enough of the target sequence that the requirements of the assay, testing, cloning or other use for the amplified nucleic acid are met. The promoter-primer is used as a template to create a complementary nucleic acid sequence extending from the 3'-end (also known as the 3' terminus) of a target nucleic acid sequence, to result in a generally double stranded promoter, subject to any denaturing or enzymatic activity that may disrupt the double strand.

A DNA- or RNA-dependent DNA polymerase also creates a complementary strand to the target nucleic acid molecule, using as a template the portion of the target sequence 5' to the complementary region of the promoter-primer.

The 3'-end of the promoter-primer may be modified, or blocked, so as to prohibit or inhibit an extension reaction from proceeding therefrom. A solution of promoter-primer comprising both modified and unmodified promoter-primer consists of essentially the same nucleic acid sequence for the purposes of the present invention. The modified promoter-primer does not contain a different promoter nor a different recognition sequence from the unmodified promoter-primer. This means that, within about 10 bases, the modified and unmodified promoter-primers are recognized by the same RNA polymerase, and recognize the same target sequence (although not necessarily at precisely the same position). In a preferred embodiment, the modified and unmodified or mixture of modified promoter-primers are identical except for the modification. The 3'-end of the promoter-primer can be blocked in a variety of ways well known to those skilled in the art. Such promoter-primers are generally between 40 and 100 bases in length, preferably between 40 and 60 bases.

F. Target Nucleic Acid Sequence, Target Sequence.

A "target nucleic acid sequence," or "target sequence," has a desired nucleic acid sequence to be amplified, and may be either single-stranded or double-stranded and may include other sequences beside 5' or 3' of the sequences to be amplified which may or may not be amplified.

The target nucleic acid sequence includes the completing sequences to which the promoter-primer hybridizes during performance of the present invention.

Where the target nucleic acid sequence is originally single-stranded, the term refers to either the (+) or (−) strand, and will also refer to the sequence complementary to the target sequence. Where the target nucleic acid sequence is originally double-stranded, the term refers to both the (+) and (−) strands.

G. Plus (+) and Minus (−) Strand(s).

Discussions of nucleic acid synthesis are greatly simplified and clarified by adopting terms to name the two complementary strands of a nucleic acid duplex. Traditionally, the strand encoding the sequences used to produce proteins or structural RNAs was designated as the "plus" strand and its complement the "minus" strand. It is now known that in many cases, both strands are functional, and the assignment of the designation "plus" to one and "minus" to the other must then be arbitrary. Nevertheless, the terms are very useful for designating the sequence orientation of nucleic acids and will be employed herein for that purpose, with the "plus" strand denominating the original target sequence strand that is completed with the promoter-primer.

H. DNA-Dependent DNA Polymerase.

A "DNA-dependent DNA polymerase" is an enzyme that synthesizes a complementary DNA copy from a DNA template. Examples are DNA polymerase I from *E. coli* and bacteriophage T7 DNA polymerase. All known DNA-dependent DNA polymerases require a complementary primer to initiate synthesis. It is known that under suitable conditions certain DNA-dependent DNA polymerases may synthesize a complementary DNA copy from an RNA template.

I. DNA-Dependent RNA Polymerase (Transcriptase).

A "DNA-dependent RNA polymerase" or "transcriptase" is an enzyme that synthesizes multiple RNA copies from a double-stranded or partially-double stranded DNA molecule having a (usually double-stranded) promoter sequence. It should be noted that the present invention includes single stranded promoters, along with the RNA polymerases that recognize them. The RNA molecules ("transcripts") are synthesized in the 5'→3' direction of the RNA molecule, beginning at a specific position just downstream of the promoter. Examples of transcriptases are the DNA-dependent RNA polymerases from *E. coli* and bacteriophages T7, T3, and SP6. Under appropriate conditions, as shown herein, some transcriptases may use RNA or an RNA:DNA copolymer as a template.

J. RNA-Dependent DNA Polymerase (Reverse Transcriptase).

An "RNA-dependent DNA polymerase" or "reverse transcriptase" is an enzyme that synthesizes a complementary DNA copy from an RNA template. All known reverse transcriptases also have the ability to make a complementary DNA copy from a DNA template; thus, they are both RNA- and DNA-dependent DNA polymerases. A primer is required to initiate synthesis with either the RNA or DNA templates.

K. RNAse H.

An "RNAse H" is an enzyme that degrades the RNA portion of an RNA:DNA duplex. RNAse H's may be endonucleases or exonucleases. Most reverse transcriptase enzymes normally contain an RNAse H activity in addition to their polymerase activity. However, other sources of the RNAse H are available without an associated polymerase activity. The degradation may result in separation of RNA from a RNA:DNA complex. Alternatively, the RNAse H may simply cut the RNA at various locations such that portions of the RNA melt off or permit enzymes to unwind portions of the RNA, or the RNA fragments generated may serve as primers for a DNA polymerase.

L. Hybridize, Complex.

The terms "hybridize" and "complex" refer to the formation of duplexes between nucleotide sequences that are sufficiently complementary to form duplexes (or "complexes") via Watson-Crick base pairing. Where a promoter-primer or primer "hybridizes" with target (template), such complexes (or hybrids) are sufficiently stable to serve the priming function required by a DNA polymerase to initiate DNA synthesis.

M. Modified Primer or Promoter-primer.

The 3'-end of the primer or promoter-primer may be modified, or blocked, so as to prohibit or inhibit an extension reaction from proceeding therefrom. A primer or promoter-primer having both modified and unmodified members consists of essentially the same nucleic acid sequence for the purposes of the present invention. In other words, the modified primer or promoter-primer does not contain a different complexing sequence (primer) in terms of its specificity in that both the modified and unmodified oligonucleotide hybridizes in effectively the same position (plus or minus about ten bases) on the target nucleic acid sequence such that amplification of the target sequence is not prohibited. Also, the modified promoter-primer does not contain a different recognition sequence (promoter) from the unmodified promoter-primer. This means that, within about 10 bases, the modified and unmodified primers or promoter-primers are the same, are recognized by the same RNA polymerase, and recognize the same target sequence (although not necessarily at precisely the same position). In a preferred embodiment, the modified and unmodified primers or promoter-primers are identical except for the modification.

The 3'-end of the primer or promoter-primer can be modified in a variety of ways well known to those skilled in the art. Appropriate modifications to a promoter-primer can include addition of ribonucleotides, 3' deoxynucleotide residues, (e.g., cordycepin (CO, Glen Research)), 3', 2'-dideoxy nucleotide residues, modified nucleotides such as phosphorothioates, and non-nucleotide linkages such as described in Arnold, et al., (PCT US 88/03173) (RS) or alkane-diol modifications (Wilk et al. Nuc. Acids Res. 18:2065, 1990) (RP), or the modification may simply consist of a region 3' to the priming sequence that is uncomplementary to the target nucleic acid. Of course, other effective modifications are possible as well.

A mixture of modified and unmodified oligonucleotides may be used in an amplification reaction, and ratios of blocked to unblocked oligonucleotide from 2:1 to 1,000:1 have been successfully used. A mixture of oligonucleotides with different 3' modifications may also be used.

DETAILED DESCRIPTION OF THE INVENTION

The present invention is directed to a method, composition and kit for the amplification of specific nucleic acid target sequences. Such amplified target sequences are useful in assays for the detection and/or quantitation of specific nucleic acid target sequences or for the production of large numbers of copies of DNA and/or RNA of specific target sequences for a variety of uses.

Figure 1:
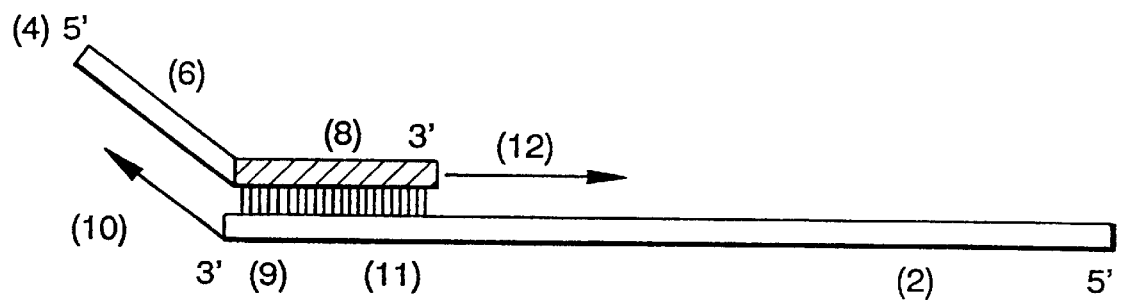
FIG. 1 depicts a promoter-primer and a target nucleic acid that has a defined 3'-end and, thus, no additional sequences 3' to the target sequence, but which does have additional sequences 5' to the target sequence. THE different elements shown in FIG. 1 are as follows: (2) nucleic acid target sequence; (4) oligonucleotide comprising a promoter-primer; (6) promoter; (8) primer; (9) 3'-end portion of the target sequence; (10) DNA extension product; (11) promoter-primer/target sequence complex; and (12) complementary strand.

Using FIG. 1 for illustration, the present invention features a method comprising treating a nucleic acid target sequence 2, which may be RNA or DNA, with an oligonucleotide 4 that comprises a promoter-primer that has a promoter 6 and a primer 8, wherein the primer 8 is sufficiently complementary to the 3'-end 9 portion of the target sequence to complex at or near the 3'-end 9 of the target sequence. The promoter-primer 4 consists essentially of only a single nucleic acid sequence, and no other promoter-primers need be introduced to the reaction mixture to achieve amplification. Promoters suitable for the promoter-primer of the present invention are nucleic acid sequences (produced naturally, synthetically or as a product of a restriction digest) that are specifically recognized by an RNA polymerase that binds to that sequence and initiates the process of transcription whereby RNA transcripts are produced. The promoter sequence may optionally include nucleotide bases extending beyond the actual recognition site for the RNA polymerase, which may impart added stability or susceptibility to degradation processes or increased transcription efficiency. Promoter sequences for which there is a known and available polymerase are particularly suitable. Such promoters include those recognized by RNA polymerases from bacteriophages T3, T7 or SP6, or from E. coli.

In some circumstances it may be desirable to introduce "helper" oligonucleotides into the mixture, which helper oligonucleotides assist the promoter-primer to complex with the target sequence.

The promoter-primer 4 and the target sequence 2 are subjected to conditions whereby a promoter-primer/target sequence complex 11 is formed and DNA synthesis may be initiated. Accordingly, the reaction mixture is incubated under conditions whereby a promoter-primer/target sequence complex is formed, including DNA priming and nucleic acid synthesizing conditions (including ribonucleotide triphosphates and deoxyribonucleotide triphosphates) for a period of time sufficient whereby multiple copies of the target sequence are produced. The reaction advantageously takes place under conditions suitable for maintaining the stability of reaction components such as the component enzymes and without requiring modification or manipulation of reaction conditions during the course of the amplification reaction. Accordingly, the reaction may take place under conditions that are substantially isothermal and include substantially constant ionic strength and pH. In other words, the reaction conditions may be effectively constant, which means that the temperature, pH and ionic concentration are not significantly, purposefully altered so as to affect the reaction conditions. The components of the reaction mixture may be combined stepwise or at once.

During performance of the reaction, the 3'-end 9 of the target sequence is extended by an appropriate DNA polymerase in an extension reaction using the promoter sequence of the promoter-primer as a template to give a DNA extension product 10 complementary to the promoter sequence. The 3'-end of the primer region of the promoter-primer is also extended in an extension reaction, using an appropriate reverse transcriptase, to form a complementary strand 12 to the target nucleic acid sequence. The resulting double stranded promoter is then used to bind the appropriate RNA polymerase, which then uses the resulting double stranded target nucleic acid sequence to produce multiple copies of single stranded RNA (which will be complementary to the (+) strand of the target sequence).

The DNA polymerase for extension of the promoter-primer must be an RNA-dependent DNA polymerase (i.e., a reverse transcriptase) when the target sequence is RNA. Concomitantly, where the target sequence comprises DNA, the DNA polymerase must be a DNA-dependent DNA polymerase. However, as all known reverse transcriptases also possess DNA-dependent DNA polymerase activity, it is not necessary to add a DNA-dependent DNA polymerase other than reverse transcriptase in order to perform the extension reaction, including where the promoter-primer is DNA and the target sequence is RNA. Suitable reverse transcriptases include AMV reverse transcriptase and MMLV reverse transcriptase.

The RNA polymerase required for the present invention may be a DNA-dependent RNA polymerase, such as the RNA polymerases from E. coli and bacteriophages T7, T3 and SP6; it is surprising that such a DNA-dependent RNA polymerase is effective when the target sequence is RNA.

In the case where the target sequence is DNA, the 3'-end of the target sequence must be defined, as in FIG. 1, to coincide approximately with the 5'-end of the primer of the primer-promoter (i.e., the target sequence must not have nucleotides extending 3' past the region complexed with the primer). Of course, such generation may also be practiced on an RNA target nucleic acid sequence. Generation of such a defined 3'-end of the nucleic acid target by chemical or enzymatic degradation or processing are known in the art.

Figure 2:
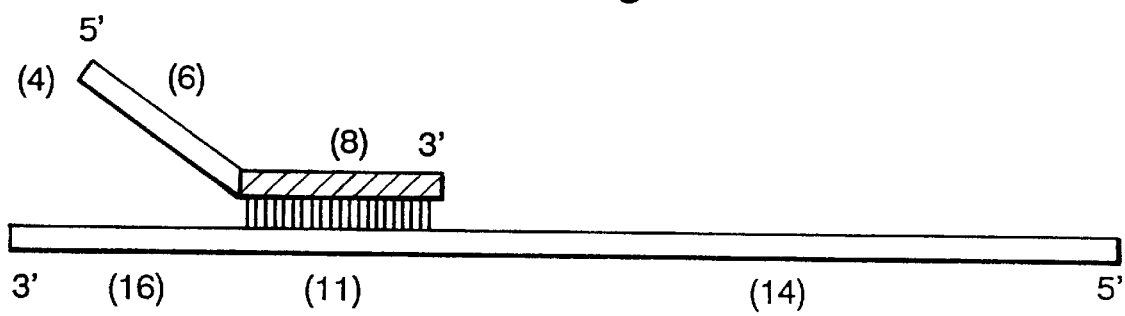
FIG. 2 depicts an RNA target sequence having additional sequences 3' to the complexing region of the target sequence. The different elements shown in FIG. 2 are as follows: (4) oligonucleotide comprising a promoter-primer; (6) promoter; (8) primer; (11) promoter-primer/target sequence complex; (14) RNA target; and (16) nucleotides extending past region 11.

As depicted in FIG. 2, the amplification may surprisingly be performed on an RNA target sequence 14 that has a strand of nucleotides 16 extending 3' past region 11 complexed with the primer.

It is a feature of the present invention that multiple copies of either DNA or RNA may be obtained.

In a preferred embodiment, the promoter-primer has a modification at its 3'-end to prevent or decrease extension from that end (along the target sequence). Methods of producing such modifications are known in the art. It is surprising that the amplification may be performed with the 3'-end so modified, and also surprising that using a mixture of modified and unmodified promoter-primer will result in higher efficiency amplification. For example, a ratio of about 150 modified promoter-primers to 1 unmodified promoter-primer has been found to greatly increase the efficiency and effectiveness of amplification. However, this ratio will change according to the reaction conditions and reagents, such as the promoter-primer and the target sequence.

In still a further aspect, the invention features a kit comprising some or all of the reagents, enzymes and promoter-primers necessary to perform the invention. The items comprising the kit may be supplied in separate vials or may be mixed together, where appropriate.

EXAMPLES

Preface

The following examples demonstrate the mechanism and utility of the present invention. They are not limiting and should not be considered as such.

The enzymes used in the following examples are avian myeloblastosis virus (AMV) reverse transcriptase, T7 RNA polymerase, Moloney murine leukemia virus (MMLV) reverse transcriptase, and Superscript (RNase H minus MMLV RT, "MMLV SC RT") from Bethesda Research Laboratories. Other enzymes containing similar activities and enzymes from other sources may be used. Other RNA polymerases with different promoter specificities may also be suitable for use.

Unless otherwise specified, the reaction conditions used in the following examples were 50 mM Tris-HCl, pH 7.6, 25 mM KCl, 17.5 mM $MgCl_2$, 5 mM dithiothreitol, 2 mM spermidine trihydrochloride, 6.5 mM rATP, 2.5 mM rCTP, 6.5 mM rGTP, 2.5 mM rUTP, 0.2 mM dATP, 0.2 mM dCTP, 0.2 mM dGTP, 0.2 mM dTTP, 0.3 $\mu$M promoter-primer, 600 units of MMLV reverse transcriptase and 400 units of T7 RNA polymerase, and specified amounts of template in 100 $\mu$l volumes. However, the best reaction conditions will vary according to the requirements of a given use and circumstances; given the present disclosure, such conditions will be apparent to one skilled in the art. The oligonucleotide sequences used are exemplary and are not limiting as other sequences have been employed for these and other target sequences.

Example 1

To demonstrate the invention using a target sequence with a defined 3'-end, a promoter-primer (Seq. ID No. 1) containing a sequence complementary to the 3' end of *Ureaplasma urealyticum* 5S rRNA, was incubated with RNA in the presence of T7 RNA polymerase and MMLV reverse transcriptase for four hours. Samples of the reaction were removed at certain timepoints and analyzed by hybridization with two probes of the same sense as the target RNA (Seq ID Nos. 2, 3) in the presence of helper probes (Seq ID Nos. 4, 5) as described in Hogan (U.S. Pat. No. 5,030,557, Means for Enhancing Nucleic Acid Hybridization).

|  | RLU | |
| --- | --- | --- |
| Time of incubation | 1 fmole target | 0.1 fmole target |
| 15 min | 5,389 | 307 |
| 30 min | 10,360 | 778 |
| 60 min | 40,622 | 5,588 |
| 120 min | 144,851 | 13,051 |
| 180 min | 192,618 | 16,249 |
| 240 min | 203,393 | 20,745 |

Example 2

To demonstrate that the invention works with a target sequence containing nucleotides 3' to the promoter-primer binding site, a promoter-primer containing sequences complementary to 21 bases of *Streptococcus pneumoniae* 16S rRNA corresponding to bases 683–703 of the *E. coli* reference sequence, (Seq ID No. 6), was incubated with 1 fmole of (+) sense *S. pneumoniae* rRNA in the presence of the following enzymes. Ten $\mu$l of the reaction was assayed with acridinium ester labelled probes of both senses (Seq ID No. 7), with helper probes (Seq ID No. 8, 9), or their complements. In a separate experiment, part of the reaction was hydrolyzed with NaOH prior to hybridization.

| Enzymes | (+) sense probe | (−) sense probe |
| --- | --- | --- |
| MMLV RT + T7 | 434,463 | 7,333 |
| MMLV SC RT + T7 | 2,617 | 3,579 |
| MMLV RT, no T7 | 2,614 | 1,733 |
| MMLV RT + T7, no primer | 1,753 | 3,840 |
| MMLV RT + T7, no NaOH | 615,299 | |
| MMLV RT + T7, + NaOH | 2,499 | |

The results show that the amplification of the present invention is dependent on reverse transcriptase, T7 RNA polymerase and RNase H activity, and that the predominant product produced is RNA complementary to the target RNA.

Example 3

Figure 3:
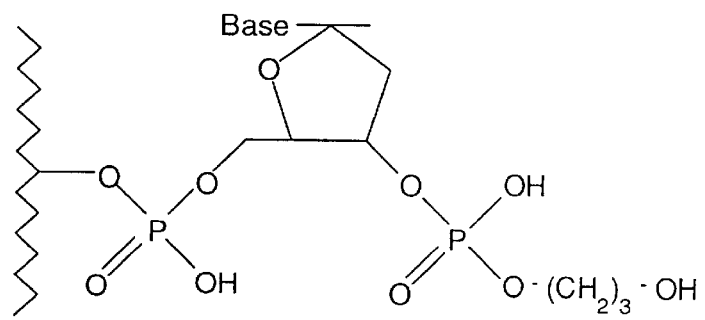
FIG. 3 is a diagrammatic representation of an alkane diol modification or RP, on an oligonucleotide (zigzag line).

To determine if extension of the 3' end of the promoter-primer was required for amplification, a promoter-primer was synthesized with 3' modifications using standard chemistry, as described by Arnold et al. (RS; PCT US 88/03173) or Wilk, et al., (RP; FIG. 3 in Nucleic Acids Res. 18:2065, 1990), or cordycepin (CO, Glen Research). The effect of these modifications on extension by reverse transcriptase was tested in the following experiment. A promoter-primer with a sequence complementary to *S. pneumoniae* 16S rRNA (Seq ID 6) was hybridized to target, then incubated in the presence of MMLV RT for 30 min. At the end of the extension reaction, the RNA and cDNA was denatured at 95° C. for two minutes, and assayed by hybridization protection assay with a probe the same sense as the rRNA (Seq ID No. 7) with helper probes (Seq ID Nos. 8, 9).

|  | RLU | |
| --- | --- | --- |
| Amount of target: | 1 pmole | 0 pmole |
| Primer: | | |
| unmodified | 756,996 | 5,038 |
| 3' RSL | 391,079 | 4,132 |
| 3' RP | 68,153 | 4,365 |
| 3' CO | 10,521 | 4,717 |

The results indicated that the 3' modifications did alter extension by reverse transcriptase relative to the unmodified primer.

Example 4

To determine if extension of the 3' end was required for the amplification of a target sequence with a defined 3'-end, the promoter-primer complementary to the 3' end of *Ureaplasma urealyticum* 5S rRNA (Seq. ID 1), was modified at the 3' end with RS, and incubated with 1 fmole of target RNA, MMLV reverse transcriptase and T7 RNA polymerase. Hybridization with probes as described in Example 1 indicated that efficient extension of the promoter-primer was not required for amplification. Reverse transcriptase activity was required, as shown by the lack-of amplification in the reaction containing only T7 RNA polymerase.

| | RLU | |
|---|---|---|
| Enzymes | unmodified | modified |
| MMLV RT + T7 | 11,189 | 12,443 |
| MMLV SC RT + T7 | 8,738 | 3,742 |
| T7 only | 1,838 | 1,694 |
| No target | 1,272 | 1,157 |

Example 5

To test the effect of 3' modifications on amplification of a target containing sequences 3' to the promoter-primer binding site, a promoter-primer containing sequences complementary to S. pneumoniae 16S rRNA, (Seq ID No. 6), was synthesized with 3' RS, 3' RP, or 3' cordycepin modification. The modified and unmodified promoter-primers were incubated with S. pneumoniae rRNA, MMLV reverse transcriptase and T7 RNA polymerase at 37° C. for 4 hr. Ten µl of the reaction was assayed with a probe of the same sense as the target RNA.

| | RLU | | |
|---|---|---|---|
| Primer | 1 fmol target | 0.1 fmol target | 0 target |
| unmodified | 39,652 | 7,952 | 2,785 |
| 3' RSL | 227,639 | 15,732 | 3,117 |
| 3' RP | 556,708 | 589,168 | 3,368 |
| 3' CO | 509,262 | 30,004 | 3,219 |

Surprisingly, the data show that modifications to the 3' end of the promoter-primer increased the signal observed with this amplification mechanism.

Example 6

The following experiment was performed to demonstrate the kinetics of accumulation of product with promoter-primers with unmodified or modified 3' ends. A promoter-primer containing sequences complementary to M. tuberculosis 23S rRNA was incubated with 1 fmole of M. tuberculosis rRNA in the presence of MMLV RT and T7 RNA polymerase. At the time points indicated, samples were removed and assayed with an acridinium ester labelled probe the same sense as the target RNA. Background RLU from target free reactions were subtracted from the data.

| Time | Unmodified | 3' RS | 3' RP |
|---|---|---|---|
| 0 min | 0 | 0 | 0 |
| 15 min | 2,266 | 430 | 43 |
| 30 min | 7,622 | 1,532 | 214 |
| 60 min | 9,349 | 9,584 | 1,403 |
| 120 min | 15,281 | 32,007 | 150,781 |
| 180 min | 24,528 | 38,086 | 590,033 |
| 240 min | 23,866 | 46,276 | 868,145 |

The data show that the unmodified and 3' RS modified promoter-primers accumulate product in a linear manner, while the 3' RP promoter-primer appears to accumulate product in a more exponential fashion. This result was also unexpected, and implies a unique amplification mechanism that occurs at essentially constant temperature, pH and ionic strength.

Example 7

In this example, different promoter-primers were incubated with S. pneumoniae rRNA for 4 hours in the presence of 600 units of AMV reverse transcriptase and 400 units of T7 RNA polymerase. Ten µl of sample were assayed with an acridinium-ester labeled probe of the same sense as the target RNA.

| | 1 fmol target | 0 fmol target |
|---|---|---|
| Unmodified | 66,042 | 3,607 |
| 3' RP | 359,597 | 3,411 |
| 3' CO | 110,260 | 2,984 |

The data show that the 3' modified promoter-primers result in higher signals than the unmodified version with AMV reverse transcriptase.

Example 8

The following experiment demonstrated that additives (DMSO and glycerol) increase the effectiveness (sensitivity) of the amplification system. Modified or unmodified promoter-primers (Seq ID No. 6) were added to S. pneumoniae rRNA in the presence of MMLV reverse transcriptase and T7 RNA polymerase and incubated at 37° C. for 4 hours. Ten µl of reaction were assayed with acridinium ester labelled probe of the same sense as the target RNA, and negative values were subtracted.

| Primer | DMSO/gly | 0.1 fmol | 0.01 fmol |
|---|---|---|---|
| unmodified | − | 3,176 | 18 |
| | + | 1,468 | 763 |
| 3' CO | − | 5,168 | 668 |
| | + | 46,915 | 3,070 |
| 3' RP | − | 83,870 | 7,400 |
| | + | 935,945 | 117,051 |

The data show that the additives had little effect on the results with the unmodified promoter-primer, but increased signals significantly with the 3' modified promoter-primers, with the most marked effect with the 3' RP version.

Example 9

In this experiment, promoter-primers with a sequence complementary to the 23S rRNA of M. tuberculosis, (Seq ID No. 10) were synthesized with one (ribo) or two (diribo) 3' terminal deoxycytidines replaced with one or two 3' ribocytidine residues, or with a 3' terminal phosphorothioate (PS) deoxynucleotide. These modified promoter-primers were used to amplify M. tuberculosis rRNA in 50 mM Tris HCl pH 8, 20 mM Mgcl$_2$, 35 mM KCl, 4 mM each GTP, ATP, UTP, CTP and 1 mM each dTTP, dGTP, dCTP, dATP, 15 mM N-acetyl-cysteine, 10% glycerol, 10% DMSO, 600 units MMLV reverse transcriptase, and 400 units T7 RNA polymerase, at 42° C. for 4 hours. Five µl of each reaction was heated to 95° C. for 2 minutes and assayed with a probe of the same sense as the rRNA target (Seq ID #11), with helper probes ID 12 and 13.

| Tmol Target: | 3,000 | 300 | 30 | 3 | 0 |
|---|---|---|---|---|---|
| Primer | | | | | |
| Unmodified | 11,162 | 1,508 | 931 | 779 | 807 |
| 3' RP | 1,901,532 | 1,494,050 | 513,419 | 14,243 | 658 |
| 3' ribo | 57,401 | 3,992 | 644 | 670 | 589 |
| 3' diribo | 34,265 | 11,459 | 1,445 | 666 | 584 |

-continued

| Tmol Target: | 3,000 | 300 | 30 | 3 | 0 |
|---|---|---|---|---|---|
| Unmodified | | 1,799 | 877 | N.T. | 782 |
| 3' PS | | 266,755 | 12,567 | 1,617 | 656 |

The results showed that promoter-primers with one or two ribonucleotides at the 3' end, or with a 3' phosphorothioate linkage, give better amplification in this system than unmodified promoter-primers.

Example 10

Another method for altering the extension of promoter-primer by reverse transcriptase was to mix unmodified promoter-primer with blocked, cordycepin-modified promoter-primer. Use of a mixture of promoter-primers would significantly decrease the production of cDNA observed in a reverse transcription reaction, as observed for other 3' modifications. The following experiment used promoter-primers with sequence complementary to M. tuberculosis 16S rRNA (Seq ID. #14), either modified with cordycepin or unmodified. The promoter-primers were incubated with 3 tmol of M. tuberculosis rRNA, 300 units of MMLV reverse transcriptase and 200 units of T7 RNA polymerase, using the same conditions as example 9 except that 10 mM trimethyl ammonium chloride was present. After a 2 hour incubation at 42° C., twenty µl of the reaction was assayed with a probe of the same sense as the target RNA (Seq ID 15, with helpers #16, 17). The results are the average of 5 replicates.

| Target | 3' CO Primer | Unmodified Primer | RLU |
|---|---|---|---|
| + | 15 pmol | 0 pmol | 1,879 |
| + | 14.9 pmol | 0.1 pmol | 191,988 |
| − | 15 pmol | 0 pmol | 1,055 |

As can be seen, a mixture of modified and unmodified promoter primer worked better than completely modified promoter primer. Varying the ratio (e.g., between 1:1 to 150:1) of modified to unmodified promoter-primer effectively increased the efficiency of amplification. The optimal ratio will change according to reaction conditions, including the reagents used, the target sequence, and the promoter-primer. Selecting appropriate conditions for a given amplification is within the skill of one skilled in the art without undue experimentation.

In a separate experiment, the signals obtained from the amplification were compared to known standards, and the degree of amplification calculated to be $2.6 \times 10^5$ fold.

Example 11

In this example, reactions were performed as in Example 10, except that the promoter primers were unmodified or modified with RP or CO. Thirty tmol target was added to each reaction. As shown, a mixture of promoter primers with different 3' modifications result in significant amplification.

| Primer | | | |
|---|---|---|---|
| 3' CO | 3' RP | Unmodified | RLU |
| 15 pmol | — | 0.1 pmol | 802,374 |
| 13 pmol | 2 pmol | — | 440,854 |

The amount of non-specific product generated was shown to be much lower with the modified primers, evidencing another advantage of the invention.

Example 12

The increase in the number of complementary copies of the target sequence with time requires reverse transcriptase and T7 RNA polymerase. When the promoter-primer hybridizes to the 3' end of a target, copying of the T7 promoter sequence results in a double-stranded DNA promoter that can be recognized by T7 RNA polymerase and utilized to make RNA copies of the target sequence. The results with the 3' modified promoter-primers implied that the T7 RNA polymerase was using RNA as a template for RNA synthesis. Synthetic oligonucleotides were made to test this hypothesis. The first oligonucleotide was a DNA promoter-primer, containing a 5' T7 promoter sequence linked to a 3' target binding sequence. Another oligonucleotide containing only the promoter sequence was also synthesized. The target sequence consisted of an RNA:DNA chimeric molecule containing 5' synthetic RNA target sequence with the DNA complement of the T7 promoter sequence attached to the 3' end.

In this experiment the 10 or 1 fmol of the RNA-DNA chimeric target was hybridized with the promoter-primer containing the T7 promoter and a target binding sequence, or the promoter sequence alone, leaving the RNA target strand single-stranded. The hybrids were incubated with or without T7 RNA polymerase and the products were hybridized with a probe of the same sense as the RNA target sequence.

| | RLU | | | |
|---|---|---|---|---|
| | 10 fmol | | 1 fmol | |
| Promoter-primer | +T7 | −T7 | +T7 | −T7 |
| Pro + target | 146,060 | 2,490 | 16,532 | 2,721 |
| pro only | 425,127 | 2,753 | 33,474 | 2,557 |

Surprisingly, the data show that an RNA fragment can be used by T7 RNA polymerase as a template for RNA transcription.

Example 13

The following experiment showed that an RNA strand can be used to synthesize RNA in the presence of reverse transcriptase and T7 RNA polymerase. In this experiment, the RNA:DNA chimeric target was compared to a synthetic RNA fragment containing only the target sequence.

| Target | T7 | RT | 10 fmole | 1 fmole |
|---|---|---|---|---|
| RNA:DNA chimera | + | MMLV | 1,369,888 | 264,864 |
| | + | AMV | 334,139 | 118,406 |
| | − | − | 5,066 | |
| RNA target | + | MMLV | 13,609 | 3,875 |
| | + | AMV | 26,318 | 4,824 |
| | − | − | 5,862 | |

The present embodiments of this invention are to be considered in all respects as illustrative and not restrictive, the scope of the invention being indicated by the appended claims rather than by the foregoing description, and all changes which come within the meaning and range of equivalency of the claims therefore are intended to be embraced therein.

What is claimed is:

1. A promoter-primer comprising the sequence of SEQ ID NO 6.

2. The promoter-primer of claim 1, wherein said promoter-primer consists of the sequence of SEQ ID NO 6.

3. A probe mix comprising:

a) a promoter-primer comprising the sequence of SEQ ID NO 6; and b) one or more helper probes each independently comprises a sequence selected from the group consisting of: SEQ ID NO 8, SEQ ID NO 9, and the RNA equivalents of SEQ ID NO 8 and SEQ ID NO 9.

4. The probe mix of claim 3, wherein said promoter-primer consists of the sequence of SEQ ID NO 6.

5. The probe mix of claim 3, further comprising a detection probe, wherein said detection probe is either an oligonucleotide comprising the sequence of SEQ ID NO 7 or the RNA equivalent thereof.

6. The probe mix of claim 4, wherein said probe mix comprises a first helper probe comprising the sequence of SEQ ID NO 8, and a second helper probe comprising the sequence of SEQ ID NO 9.

7. The probe mix of claim 6, wherein said first helper probe consists of the sequence of SEQ ID NO 8, and said second helper probe consists of the sequence of SEQ ID NO 9.

8. The probe mix of 7, further comprising a comprising a detection probe, wherein said detection probe is an oligonucleotide comprising the sequence of SEQ ID NO 7 or the RNA equivalent thereof.

9. The probe mix of claim 7, wherein said detection probe consists of the sequence of SEQ ID NO 7 and one or more optionally present detectable labels.

10. A probe mix comprising
   a) promoter-primer comprising the sequence of SEQ ID NO 6 and
   b) a detection probe comprising the sequence of SEQ ID NO 7 or the RNA equivalent thereof.

11. The probe mix of claim 10, wherein said promoter-primer consists of the sequence of SEQ ID NO 6.

12. The probe mix of claim 11, wherein said detection probe consists of the sequence of SEQ ID NO 7 and one or more optionally present detectable labels.

13. A method of amplifying *S. pneumoniae* rRNA present in a sample comprising the steps of contacting said sample with a promoter-primer comprising the sequence of SEQ ID NO 6 and amplifying said *S. pneumoniae* rRNA nucleic acid.

14. The method of claim 13, wherein said promoter-primer consists of the sequence of SEQ ID NO 6.

15. A method of determining whether *S. pneumoniae* may be present in a sample comprising the steps of:
   a) amplifying *S. pneumoniae* nucleic acid present in said sample using a promoter-primer comprising the sequence of SEQ ID NO 6 to produce amplified nucleic acid; and
   b) detecting the presence of said amplified nucleic acid as an indication of the presence of *S. pneumoniae*.

16. The method of claim 15, wherein said promoter-primer consists of the sequence of SEQ ID NO 6.

17. The method of claim 16, wherein said amplified nucleic acid is detected using a detection oligonucleotide comprising the sequence of SEQ ID NO 7 or the RNA equivalent thereof.

18. The method of claim 17, wherein said detection oligonucleotide consists of the sequence of SEQ ID NO 7 and an optionally present detectable label.

19. The method of claim 18, further comprising the use of one or more helper probes each independently comprising a sequence selected from the group consisting of: SEQ ID NO 8, SEQ ID NO 9, and the RNA equivalents of SEQ ID NO 8 and SEQ ID NO 9.

20. The method of claim 19, further comprising the use of a first helper probe consisting of the sequence of SEQ ID NO 8; and second helper probe consisting of the sequence of SEQ ID NO 9.

\* \* \* \* \*

UNITED STATES PATENT AND TRADEMARK OFFICE
CERTIFICATE OF CORRECTION

PATENT NO. : 5,888,729
DATED : March 30, 1999
INVENTOR(S) : Daniel L. Kacian, et. al.

It is certified that error appears in the above-identified patent and that said Letters Patent is hereby corrected as shown below:

Column 22, Line 59: delete "comprises" and insert --comprising--.

Column 23, Line 9: delete "mix of 7" and insert --mix of claim 7--.

Column 23, Line 9: delete "comprising a comprising a" and insert

--comprising a--.

Column 23, Line 16: delete "comprising" and insert --comprising:--.

Column 23, Line 18: delete "NO 6" and insert --NO 6;--.

Signed and Sealed this

Fourteenth Day of December, 1999

Attest:

Q. TODD DICKINSON

Attesting Officer

Acting Commissioner of Patents and Trademarks

SEQUENCE LISTING ( 1 ) GENERAL INFORMATION:

( i i i ) NUMBER OF SEQUENCES: 17

( 2 ) INFORMATION FOR SEQ ID NO: 1:

( i ) SEQUENCE CHARACTERISTICS:
        ( A ) LENGTH: 53
        ( B ) TYPE: nucleic acid
        ( C ) STRANDEDNESS: single
        ( D ) TOPOLOGY: linear ( i i ) SEQUENCE DESCRIPTION: SEQ ID NO: 1:

AATTTAATAC GACTCACTAT AGGGAGAGCG TAGCGATGAC CTATTTTACT TGC    53

( 2 ) INFORMATION FOR SEQ ID NO: 2:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( i i ) SEQUENCE DESCRIPTION: SEQ ID NO: 2:

CGAACACAGA AGTCAAGCAC TCTAGAGCCG    30

( 2 ) INFORMATION FOR SEQ ID NO: 3:

( i ) SEQUENCE CHARACTERISTICS:
        ( A ) LENGTH: 36
        ( B ) TYPE: nucleic acid
        ( C ) STRANDEDNESS: single
        ( D ) TOPOLOGY: linear ( i i ) SEQUENCE DESCRIPTION: SEQ ID NO: 3:

GTGATCATAT CAGAGTGGAA ATACCTGTTC CCATCC    36

( 2 ) INFORMATION FOR SEQ ID NO: 4:

( i ) SEQUENCE CHARACTERISTICS:
        ( A ) LENGTH: 34
        ( B ) TYPE: nucleic acid
        ( C ) STRANDEDNESS: single
        ( D ) TOPOLOGY: linear ( i i ) SEQUENCE DESCRIPTION: SEQ ID NO: 4:

GTAGTGATCA TATCAGAGTG GAAATACCTG TTCC    34

( 2 ) INFORMATION FOR SEQ ID NO: 5:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) SEQUENCE DESCRIPTION: SEQ ID NO: 5:

GCAAGTAAAA TAGGTCATCG CTACGC    26

( 2 ) INFORMATION FOR SEQ ID NO: 6:

( i ) SEQUENCE CHARACTERISTICS:
        ( A ) LENGTH: 48
        ( B ) TYPE: nucleic acid
        ( C ) STRANDEDNESS: single
        ( D ) TOPOLOGY: linear ( i i ) SEQUENCE DESCRIPTION: SEQ ID NO: 6:

AATTTAATAC GACTCACTAT AGGGAGACTA CGCATTTCAC CGCTACAC 48

( 2 ) INFORMATION FOR SEQ ID NO: 7:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 7:

GGCTTAACCA TAGTAGGCTT TG 22

( 2 ) INFORMATION FOR SEQ ID NO: 8:

( i ) SEQUENCE CHARACTERISTICS:
        ( A ) LENGTH: 39
        ( B ) TYPE: nucleic acid
        ( C ) STRANDEDNESS: single
        ( D ) TOPOLOGY: linear ( i i ) SEQUENCE DESCRIPTION: SEQ ID NO: 8:

GAGCGCAGGC GGTTAGATAA GTCTGAAGTT AAAGGCTGT 39

( 2 ) INFORMATION FOR SEQ ID NO: 9:

( i ) SEQUENCE CHARACTERISTICS:
        ( A ) LENGTH: 36
        ( B ) TYPE: nucleic acid
        ( C ) STRANDEDNESS: single
        ( D ) TOPOLOGY: linear ( i i ) SEQUENCE DESCRIPTION: SEQ ID NO: 9:

GAAACTGTTT AACTTGAGTG CAAGAGGGGA GAGTGG 36

( 2 ) INFORMATION FOR SEQ ID NO: 10:

( i ) SEQUENCE CHARACTERISTICS:
        ( A ) LENGTH: 47
        ( B ) TYPE: nucleic acid
        ( C ) STRANDEDNESS: single
        ( D ) TOPOLOGY: linear ( i i ) SEQUENCE DESCRIPTION: SEQ ID NO: 10:

AATTTAATAC GACTCACTAT AGGGAGACCA GGCCACTTCC GCTAACC 47

( 2 ) INFORMATION FOR SEQ ID NO: 11:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) SEQUENCE DESCRIPTION: SEQ ID NO: 11:

GGAGGATATG TCTCAGCGCT ACC 23

( 2 ) INFORMATION FOR SEQ ID NO: 12:

( i ) SEQUENCE CHARACTERISTICS:
        ( A ) LENGTH: 38
        ( B ) TYPE: nucleic acid
        ( C ) STRANDEDNESS: single
        ( D ) TOPOLOGY: linear ( i i ) SEQUENCE DESCRIPTION: SEQ ID NO: 12:

```
CGGCTGAGAG  GCAGTACAGA  AAGTGTCGTG  GTTAGCGG                                              3 8
```

( 2 ) INFORMATION FOR SEQ ID NO: 13:

( i ) SEQUENCE CHARACTERISTICS:
        ( A ) LENGTH: 36
        ( B ) TYPE: nucleic acid
        ( C ) STRANDEDNESS: single
        ( D ) TOPOLOGY: linear ( i i ) SEQUENCE DESCRIPTION: SEQ ID NO: 13:

```
GGGTAACCGG  GTAGGGGTTG  TGTGTGCGGG  GTTGTG                                                3 6
```

( 2 ) INFORMATION FOR SEQ ID NO: 14:

( i ) SEQUENCE CHARACTERISTICS:
        ( A ) LENGTH: 55
        ( B ) TYPE: nucleic acid
        ( C ) STRANDEDNESS: single
        ( D ) TOPOLOGY: linear ( i i ) SEQUENCE DESCRIPTION: SEQ ID NO: 14:

```
GAAATTAATA  CGACTCACTA  TAGGGAGACC  ACAGCCGTCA  CCCCACCAAC  AAGCT                         5 5
```

( 2 ) INFORMATION FOR SEQ ID NO: 15:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) SEQUENCE DESCRIPTION: SEQ ID NO: 15:

```
  GTCTTGTGGT  GGAAAGCGCT  TTAG                                                            2 4
```

( 2 ) INFORMATION FOR SEQ ID NO: 16:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) SEQUENCE DESCRIPTION: SEQ ID NO: 16:

```
  CCGGATAGGA  CCACGGGATG  CAT                                                             2 3
```

( 2 ) INFORMATION FOR SEQ ID NO: 17:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) SEQUENCE DESCRIPTION: SEQ ID NO: 17:

```
  CGGTGTGGGA  TGACCCCGCG                                                                  2 0
```